US012332228B2

(12) United States Patent
Postrel (10) Patent No.: US 12,332,228 B2
(45) Date of Patent: Jun. 17, 2025

(54) VOLATILE ORGANIC COMPOUND BIO-SCANNING SYSTEM FOR FOOD CHAIN SAFETY AND SECURITY

(71) Applicant: Richard Postrel, Miami Beach, FL (US)

(72) Inventor: Richard Postrel, Miami Beach, FL (US)

( * ) Notice: Subject to any disclaimer, the term of this patent is extended or adjusted under 35 U.S.C. 154(b) by 265 days.

(21) Appl. No.: 17/609,136

(22) PCT Filed: Jun. 8, 2021

(86) PCT No.: PCT/US2021/036276
§ 371 (c)(1),
(2) Date: Nov. 5, 2021

(87) PCT Pub. No.: WO2022/271140
PCT Pub. Date: Dec. 29, 2022

(65) Prior Publication Data
US 2024/0027413 A1    Jan. 25, 2024

Related U.S. Application Data

(60) Provisional application No. 63/035,697, filed on Jun. 6, 2020.

(51) Int. Cl.
*G01N 33/00*     (2006.01)
*A61L 2/10*      (2006.01)
*A61L 2/20*      (2006.01)

(52) U.S. Cl.
CPC ............ *G01N 33/0047* (2013.01); *A61L 2/10* (2013.01); *A61L 2/20* (2013.01); *A61L 2202/25* (2013.01)

(58) Field of Classification Search
CPC ......... G01N 33/0047; A61L 2/10; A61L 2/20; A61L 2202/25
(Continued)

(56) References Cited

U.S. PATENT DOCUMENTS 6,488,635 B1 * 12/2002 Mottram ................ A61B 5/097
                                                119/14.01
8,629,770 B2 * 1/2014 Hummer .............. G08B 25/012
                                                340/539.1

(Continued)

*Primary Examiner* — Kerri L McNally (57) ABSTRACT

Disclosed is a device for testing or screening individuals for symptoms of disease, exposure to restricted chemical or bio-hazards. The device may be configured as a compact box or tubular assay chamber. A sluice or walkway is provided for assaying moving animals. The present device assays volatile compounds, especially volatile organic compounds (VOCs) emitting from a subject individual. Different VOCs are produced as metabolic activity changes as an individual addresses a pathogenic, chemical or biological stress or progresses through normal biologic cycles such as sleep-wake, seasonal, fertility, etc. The system is especially advantageous for timing breeding events and apportioning feed for desired levels of milk production and calf health. Nanosensor elements within the device provide assessment of multiple VOCs to a system with integrated analysis capacities that rapidly compares instant data to a developed database. This comparison allows rapid assessment of metabolic or health status and potential risks the individual or offspring of the individual may face.

44 Claims, 1 Drawing Sheet

(58) Field of Classification Search
USPC ......................................................... 340/540
See application file for complete search history.

(56) References Cited

U.S. PATENT DOCUMENTS

| | | | |
|---|---|---|---|
| 2007/0292305 A1* | 12/2007 | Dempsey | A61L 2/206 |
| | | | 422/33 |
| 2009/0040044 A1* | 2/2009 | Chiao | G08B 21/0208 |
| | | | 340/540 |
| 2016/0334381 A1* | 11/2016 | King-Smith | G01N 33/0047 |
| 2017/0064929 A1* | 3/2017 | Yakovenko | A01K 1/031 |
| 2018/0232689 A1* | 8/2018 | Minvielle | G06T 7/194 |
| 2019/0183097 A1* | 6/2019 | Couse | G01S 13/0209 |

* cited by examiner

VOLATILE ORGANIC COMPOUND BIO-SCANNING SYSTEM FOR FOOD CHAIN SAFETY AND SECURITY

The present invention provides a bio-scanning system configurable for chambers or zones relevant to food supply and processing and the animal products involved in our diets. Crossover applications include applying the features related to animal derived foods to other animals such as those in zoos, preserves, and our homes. Health status of persons associated with animals, e.g., food processors, trainers, handlers, etc., may be assessed as they work, and/or enter or leave work. An assay device of the present invention can be set up in an open air zone, an enclosed paddock, corral, stable, or room, a chute, a station-such as for shade, feeding, or watering, (hereinafter collectively referenced as "chamber"). The device rapidly and non-invasively screens or probes individual zones, animals, or groups of animals for many traits including, but not limited to gender, maturity, estrus status, disease, exposure to hazards such as environmental, water or feed contaminants, bio-threats, etc. The chamber size/configurations and applications may be adapted for a broad range of operations including, but not limited to those associated with: farming, agribusiness, breeding, transport, trucking, feedlots, docks, food processing facilities, supermarkets, abattoirs, etc. The predominant improvements enabling the device features comprise a series of novel applications of nanosensor technology. The high degree of specificity, speed, and repeatability of the formats of embodiments of these devices (PROBES or PROBE) meet the requirements necessary for acceptance and commercialization of assay devices that assay volatile compounds (VOCs). The present invention enables rapid detection of volatile compounds, especially volatile organic compounds, in a time and cost-efficient manner necessary for commercialization of high-throughput operation.

The Probe has applications in a variety of fields including, but not limited to: animal health assessment, toxic exposure, bio-hazards, meat grading, hormonal treatment, foreign/non-organic additives, food storage anomalies, meat aging, cheese production—milk source, fat/protein content and aging, medical sequestration, nutrition adequacy, stage of development, etc. VOCs emitted from workers in the plants processing food can be monitored in the plant or upon entry or exit. Food safety concerns may thereby be improved. The methods and devices of the present invention allow rapid nano-assay of compounds emitted even in extreme low concentrations from an animal, an animal product, or animal associated person or item (hereinafter simplified to "subject") within the scanning area or chamber. The nanosensor elements featured in the devices are capable of extremely dense packing to thereby allow assays of an exceptionally large plurality of volatile organic and other compounds.

BACKGROUND

Security concerns have led to development of touch-free frisk devices, such as metal detection and radio signal detection wands, as well as full body scanning devices. Since the early 1970s many airports and other locations wishing to screen for weapons such as courts and legislatures installed initial screening protocols involving walking through a short metal detection tunnel. Passengers who were flagged by this initial screen then were screened with a wand device to locate the source of the alert. Sensor and information processing improvements enable similar group or mass screenings to be applied in a dynamic environment that does not require the subject to be still (like for an MRI) or in an enclosed encapsulating format.

The probes of the present invention include adaptations applicable to maturing animals and animals in transit, workers interacting with the animals, animal products, workers interacting with animal products, food products, etc. Individuals may be individually assayed for example by isolation using a barricade such as a gate or door, simply spacing subject individuals out directing subjects though a sluice or chute outfitted with sensing probes, etc. Animal handling often involves sluice or chute like paths or corridors where animals progress in a single file. The Probe is compact enough to be installed in these environments and thus is able to piggy-back on regular practices. Installing these can increase efficiency and safety while decreasing costs.

The background of these devices is provided for context. The device of the present invention while similar in shape and appearance to some familiar devices operates using enhanced monitoring principles.

BRIEF DESCRIPTION

Figure 1:
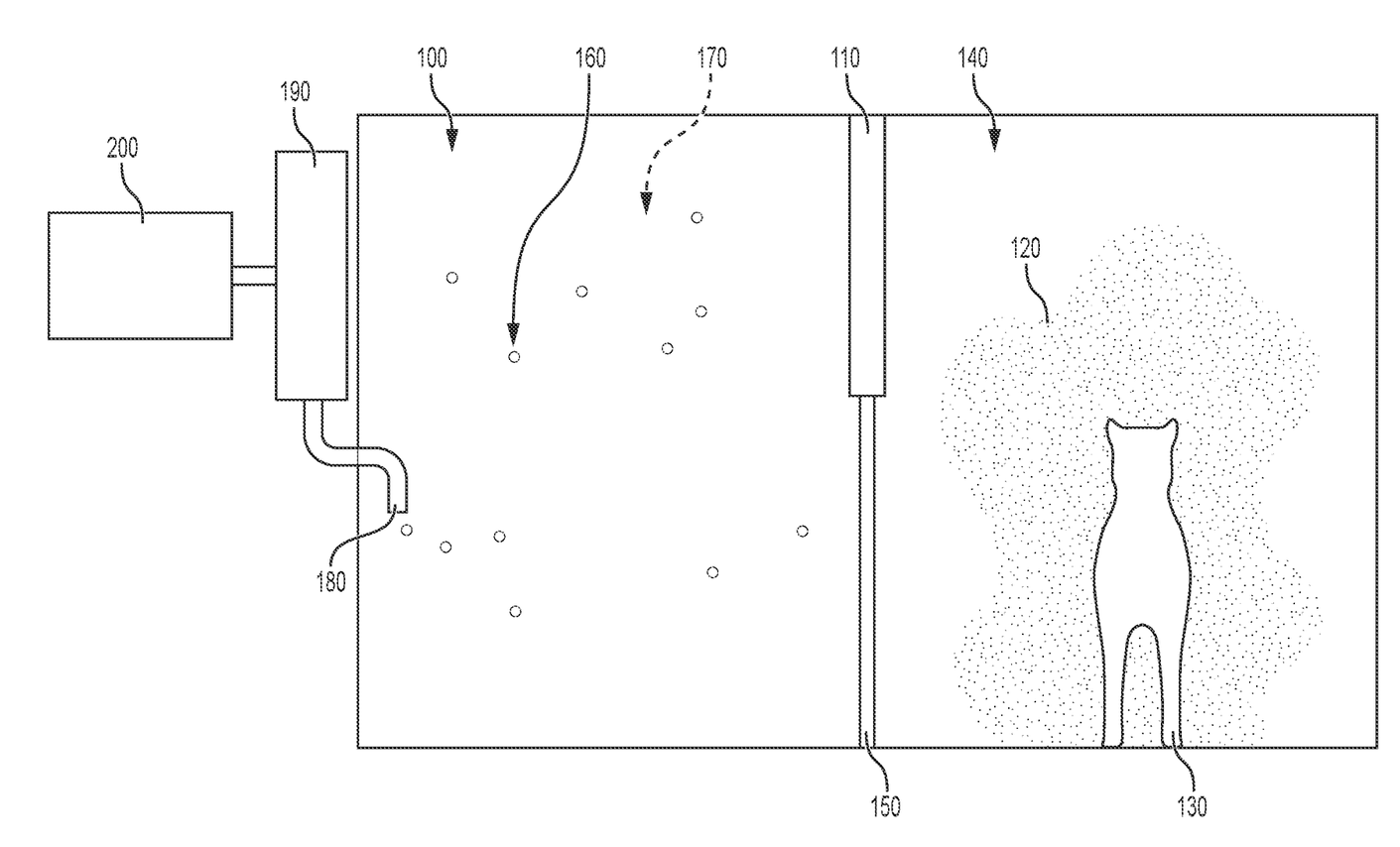
The FIGURE shows a chamber 100 with a barrier 101 that defines and isolates an internal gaseous environment 120 that surrounds a subject 130 from the volume outside the chamber 140. The barrier includes a port 150 that allows ingress and egress of the subject 130. The chamber A houses an internal array 160 of nanosensor elements (NSEs) 170 for sensing volatile compounds (not visible). A gas directing mechanism 180 moves gas (not visible) across NSEs H in the internal array 160. These feed a system 190 for collecting data from the NSEs 180 which feeds a system 200 for compiling and analyzing the data.

The present device provides a chamber for isolation of an animal, a group of animals, and/or animal associated person or item, or an animal product, (collectively referred to as "subject") to be tested. The assay chamber comprises sensor elements that detect and or quantify (assay) volatile compounds in the gaseous environment surrounding a subject. The chamber may physically isolate subjects using tactile barricades or in some embodiments the barricade(s) may comprise a space, a linear separation, or volume of ambient gas (generally air), in an environment where moving gasses move from and across the subject. The chamber device will assay gas emissions (volatile compounds, generally volatile organic compounds (VOCs)), produced by individual subjects or a plurality of subjects within the defined chamber zone. The chamber design features nanosensor elements (NSEs) aligned within the chamber so that the subject's infinitesimal, almost trace, volatile emissions are brought in contact with the sensors. The "nano" in nano sensor can have two connotations. On the one hand, the sensor may be extremely sensitive, sensing in the parts per billion (nano or $10^{-9}$) range or less. Generally, such sensors are constructed using nano-technology. Non-NSE sensors may also be present; e.g., sensors to monitor mass, height, width, length, color, etc. Though such sensors may be extremely small, generally sub-micron ($<10^{-6}$ m) in size, nano-sensors may be designed to present a large sensing surface, e.g., multi-micron, multi-mm, etc., to increase sensitivity, reliability, probability of contact with the assay target compound (VOC molecule), etc. The actual effective sensing size can be nanoscale or can be expanded to cover multi-micron or larger thickness and area dimensions. For example, a minimum dimension may be in the nano range dimensions larger than 1 Ångström (Å) (0.1 nm) into multi-millimeter range.

The subject enters or is propelled into the chamber, e.g., a sluice, a guideway, a revolving platform chamber or advancing chamber (e.g., for speed control), the cargo area of a truck, cart, container, a freezer, smokehouse, refrigerator, storehouse, etc. The portion allowing ingress and egress can include a chamber body that is elevated. The ingress-egress portion may include a barricade portion of the chamber body that is elevated from below. It may include at least one slidable portion of the chamber body that is lifted, dropped or rotated. At least one portion for allowing ingress and/or egress comprises at least one, preferably two, that are openable. Embodiments include formats where one or both egress can serve as an ingress port. Preferably the system for compiling and analyzing data is configured to select and open one egress port when predetermined criteria are satisfied. The chamber may be configured with or include two separated external zones providing access to first and second egress zones through communication with the first and second egress ports, respectively. The chamber may be sluice shaped; it may be configured as a pen, cage, stall, or crate. The chamber barrier may comprise a partition in a revolving structure that controls communication or access between at least a first zone and a second zone external to the chamber; a switching mechanism controlling access by the subject to at least one of the zones is preferred. In a preferred embodiment, the switching mechanism is controlled by a human with access to the analyzed data. The chamber may include a sluice, chute or walkway that tapers from wider to narrower in the direction of subject progression. Air or gas flows are controlled at the periphery or within the chamber to flush volatile compounds off the subject and to direct flows into contact with at least a subset of an internal array of the NSEs. The chamber may be relatively immobile or static; it may be mobile; mobility may follow or traverse a horizontal path; a; ringed shaped array may feature a system for propelling gas towards a subject; it may be in a vertical or horizontal configuration. A storehouse, such as used for aging cheeses or meats may include a probe in exhaust ventilation, a probe moving through the storehouse, or probes in static proximity to stored subjects, rooms of subjects, shelves or zones. Directed flows across a probe may be modulated by any appropriate means including, but not limited to any one or a combination of: pressure, diffusion, electrostatic charge, nozzle orifice and shape, etc. to provide the desired flow rates, zonal velocities, volume, shape (e.g., vortex). Such flow or flows may be directed between events to flush the chamber to remove background compounds from the assay volumes to reduce or minimize non-subject produced NSEs. Directing gas including the volatile compounds under assay to the NSEs may involve on or more of a plurality of stimulations. A sanitation, disinfection, or sterilization system may be included; such system may involve a light source emitting in at least one wavelength in a range from about 200 nm to about 280 nm; it may feature a light source emitting in the infrared range. The light source may be selected to emit in at least one wavelength selected for absorption by a chemical bond selected from the group consisting of: O—H, C—H and N—H; it may include at least one resistive heating element. The design choice made by one skilled in the art will select from the variety of scanning mechanisms and techniques useful in the art to achieve a 3D representation of scan results to identify specific zones of interest. When a scan has a time component, for example, several breaths of the subject, reads separated e.g., by minutes, days, months, years, etc., the subject movement and/or periodic detection data may be included to provide a 4-dimension visual, tabular, or other output relevant to maturation, growth, development, spoilage, etc.

In some embodiments e.g., in a stall or veterinary clinic, an aging facility, the subject will remain static, in a three-dimensionally enclosed environment. In some embodiments, the enclosure may be incomplete, e.g., having an open top (roof) or side panels. Several embodiments feature a mobile chamber or a chamber assaying a mobile subject. Chambers may feature one or a plurality of constraints for controlling subject movement. Such constraints may be chosen to securely prevent or greatly reduce appendage movement for example, to prevent leg movements such as kicking, neck movement, climbing, bucking, etc. A constraint may be designed to allow access to a body part, such as for an injection, inspection, biopsy, etc.

Chambers may be for groups, e.g., a subject mover compartment for an individual or a group of individuals, boxes, packages holding food, rooms, containers, etc. A static chamber may be configured as a walkway or carriageway where a subject is guided to walk or is transported through one or more chamber zones or may simply await subjects to be deposited, e.g., for monitoring ripening or aging. For example, at an entrance to a processing area a subject might be induced to step through an intermittent door opening, through a chute or walkway. As the subject animal progresses or is progressed, the subject traverses through one or more chamber(s)/zone(s) for assessment.

When entering the chamber, the subject might pass through dynamic air brushing cleansing flows or air curtain barricades that force gas over and past the subject to refresh the air carried into the chamber. These gases may be separately assayed for historical or control purposes. Another portion of the chamber comprises propelling and/or hoovering orifices that direct volatile compounds from the subject to sensor elements. On a standway or conveyor, the chamber may progress along the path with the subject or the conveyor may move the subject through one or more assay chamber(s). The chamber may encompass the entire height of the subject or may be limited to a selected subject zone such as a package vent, or animal part, e.g., below the knee, the torso, below the waist, haunches, abdomen, rib area, head, neck, head and neck, etc. or may be limited to selected height zones, e.g., arbitrarily, a shelf section, the bottom of a storage bin, the floor (drippings or droppings), etc. Such chamber may have one or more open sides or an open top or may appear in a tunnel format or a completely sequestered long term storage facility.

In a preferred complete probe, chamber hardware will incorporate or have access to at least one analytical/computational system that can store the assay information and, when present, data from non-NSE sensors or other source inputs which may include, but be not limited to: manually or automatically inputted data, results of assays other assays, conditions of the assay, such as mass of subject, source of the subject, type of product, targeted date of sale, steps/stages of assay processes, chamber integrity, chamber functions activated, chamber and chamber components movements, volumes in flux, fluxes where interacting with sensors, genetic provenance of the subject, specific NSEs activated at any stage, ingredients added, vaccination history, operator identification, subject movements, subject identifying information, subject health information, time, elapsed time, etc.

A preferred format incorporates a hoop, arch or ring or plurality thereof inside a chamber to position NSEs. The ring may be incorporated within, attached to or independently fixed or independently movable within the chamber. Aesthetically and for simplicity in shape, the chamber may be a walled walkway, an arch shaped or cylindrical like passageway or in special instances an enclosed, perhaps ring or oval shaped structure, serving to support or confine the sensor arrays. A walkway may feature multiple curves to visually isolate subjects. The probe arrays may be set in preferred locations, e.g., the head and/or hind quarters of an animal in a stall. The stall or chamber may have multiple flanks of assay strips that may be individually selected for the desired body zone of the animal.

However, the shape or zone of the assay chamber is not an essential feature of the present invention. A box shape, ellipse, hexagonal, pentagonal, octagonal, triangular, oval, circular, or other shapes may be used depending on intended purpose. The shape may taper from wider to narrower to guide an ambulating subject into a more concise area. The shape may be configured to correspond to the animal of interest. For example, a pet sized pen, cage or crate may be small for a rodent subject, larger for a cat or dog, and so on for larger dogs or cats or preserve or zoo animals. The shape may be configured as a stall enclosure for e.g., horses, an open stall, e.g., for feeding and/or milking cattle, goats, etc. The shape and size may be adjustable in any desired dimension to accommodate different sized subjects. During a probe operation, an animal may be feeding, being milked, being inseminated, being vaccinated, etc.

A user interface for monitoring and controlling function may be integral or remote. Actuation may be automated by sensors detecting, e.g., mass, motion, heat or the like to initiate data collection. The sensors may be continuously active or may be under control of a remote or local operator.

NSEs carried on the chips can be any properly designed sensing surface capable of, for example, field-effect transistor (FET) or other physico-electrical property/activity including, but not limited to: semi-conducting nano-wires, carbon nano-tubes—including single-wall carbon nano-tubes, chitosan-cantilever based, synthetic polymers—including dendrimers, plasmon resonance nano-sensors, Förster resonance energy transfer nano-sensors, vibrational phonon nano-sensors, optical emitting, optical frequency (or wavelength) based nano-sensors (sensitive to photon transmittance, absorption, reflection, energy modulation, etc.). NSE devices can be constructed from different formats, including, but not limited to: conductive polymers, single wall nanotubules, graphene, etc. Nano FETs and other nano-sensor formats generally operate by changing electrical properties as a substance comes in close proximity to the sensor by perturbing the steady state (absent the proximal substance) charges and movements (distribution of electrons) within the nano-sensor. A transistor's effective electrical properties causing an observable change in electron flow (current) sensor competence is manifest. A transistor is one example of NSE format. The present invention is not restricted to this example, but may advantageously use other electronic control devices including, but not limited to: a 2 terminal, a 3 terminal, a 4 terminal, etc. electronic signal device's sensing signal. The altered distribution of electrons, depending on the design of the nano-sensor, changes one or more electrical properties, e.g., impedance, resistance-conductivity, capacitance, inductance, etc. and thus the physical movement of a detectable particle, e.g., an electron, a photon, a phonon, a bipolaron, etc.

The chamber provides an enclosed or an isolated environment that isolates the subject for assay. Enclosed embodiments feature a chamber that has at least one opening that allows a subject to gain entry or exit in accordance with assay design and performance. When closed, the opening isolates the subject from the external environment. The opening form may be any available design function, including, but not limited to: lifting the entire chamber sides to allow a subject access to a base inside the chamber, lifting a portion of the chamber that acts as a door, sliding vertically or horizontally a portion of the wall of the chamber to act as a sliding door, opening the chamber with horizontally aligned hinges to raise or lower a door, opening the chamber horizontally with vertically aligned hinges, raising or lowering a lever constraint, etc.

Open chamber embodiments such as a conveyor or moving walkway may be open or covered at the top. Such walkways may feature box shaped rings, including those missing a top and/or bottom. A single linear array or curved array on one side of the chamber will be sufficient for some embodiments. A subject may be still on the belt or conveyor or may be ambulating. Belt systems may feature markings to cue the operator to maintain subject distancing. Prods or tapering walls or roofs may be used encourage or slow subject mobility. When used as a walkway strip, signal lights may be used rather than static markings. For example, when a subject might be overtaking another or simply approaching too close, an audible alarm may be directed to slow a trailing subject or speed the lagger, and/or the streaming lights may change intensity, pace or color to gain subject attention to modify subject speed and/or to alert an operator.

The chamber will be self-contained in that it will have only minimal interfering or non-interfering interaction with the external environment during assay procedures. When the chamber is self-contained and enclosed, pressure within the chamber is independent of the ambient temperature; inside may be the same as, positive, or negative with respect to the outside. Humidity may be modulated by controlled flow of chamber gasses, temperature control, humidification and/or de-humidification. Some versions of the chamber may include adaptable lighting including bright sunlight colors night sky or darkness, when desired to calm or to excite a subject or to emphasize or highlight for an operator one or more assay features, e.g., timing of the assay, physical area being targeted, portion of the ring being activated, providing instruction to operator, indicating progress or function, etc. Sound dampening using active or passive noise reduction may also be featured when noise is an irritant to operator or subject or impediment to subject action.

A system to map a subject in 3 spatial dimensions may be incorporated into a report so that a graphical presentation showing source or various detected compounds in available. While a detailed image is readily available using magnetic resonance or CT scans, since the VOCs escape through the skin or body orifices, internal topography is not necessary rendering these expensive methods unpreferred. A digital camera moving vertically and horizontally around the subject provides sufficient detail in multiple 2D images for a stereoscopic reconstruction of the entire surface when photos from multiple angles are present. A probe set-up may be mounted on such a drone in place of or in association with a camera or other monitoring device.

An alternate method uses air flow changes in contact with the subject body to provide a three-dimensional rendering of the body's surface. When combined with the site specified source(s) of volatile compounds the subject, operator, or other interested person(s) can visually interpret sources of each identified compound or class of compounds.

Some animals, especially pets, may exhibit anxiety or other discomfort in a partially confined or an enclosed environment. Adaptable lighting as referenced above is one potential tool for reducing anxiety. The NSEs in the chamber can be used to provide feedback as anxiety associated VOCs are monitored. The device may cycle through feedback processes to reduce such discomfort or anxiety. In some embodiments VOCs such as spice smells may be introduced. These scents may be used in feedback processes to optimize subject comfort. Spices including, but not limited to: peppermint, cinnamon, chamomile, lavender, lemon, sandalwood, rosemary, jasmine, bergamot, vanilla, Christmas tree, etc., have been suggested for calming applications. The device might also be applied in a scientific setting to monitor VOCs in response to an event under study, including, but not limited to: a frightening movie scene; a sound such as: a tone or tune, a selected pitch or chord, a language, etc.; food fragrance; color schemes; pollen; insect parts; animals; dander; suspect foods; etc.

Machine learning algorithms are ideally updated periodically by applying data obtained in conjunction with experience across groups of such devices, market needs or changes and meeting needs or desires of animal owners. For example, using data from each device, sensitivity can be adjusted for each NSE or for any subset of NSEs in accordance with self-calibration principles. The experience of a single device at its location may be used to calibrate other functions, such as ideal rate of movement, pulsing, etc., of a movable NSE or intensity of gas propulsion or strength of vacuum. Program updates may be periodically distributed to each machine as is common with modern electronics. Individual devices may be interconnected in a data-sharing system preferably available for artificial intelligence/machine learning technology that may continuously send messages, updates, or alerts to relevant recipients, perhaps recognizing inefficient or better directed coding, maintenance requirements, etc. Other interactions may signal patterns of potential new disease threats in a herd at a very early stage, even when characteristics causing or underlying the disease are not dramatic.

In a diagnostic mode, especially for pets, the chamber may be used to rapidly assess responses to environmental influences, e.g., introducing a compound, smell, stimulus (light, sound, odor, etc.) to screen for contributory factors or causes of inappropriate behavior, allergies, seizures, anxiety, etc. The chamber when used in this manner can provide early diagnostic screening methods that would greatly improve a subject's and subject's owner's experiences by foregoing invasive and prolonged testing regimes. The result will be greatly improved pet owner satisfaction and treatment outcomes.

Such device may also have applications for screening animals access to a home, business, port, country, care facility, etc., for a rapid assessment of potential contagion, avoidance of allergic response, identification of repeat lodgers, potential previous association of the pet with hazardous materials, etc. Some chamber embodiments or probe set-ups may be configured to accept persons with a pet.

A gas is flushed or otherwise caused to flow through the chamber to purge, to remove or to clear compounds that enter the chamber with the ambient atmosphere. Flushing/clearance may be accomplished in a manner chosen by the operator or device designer. For example, the base may include ports that exhaust cleansing air/gas with the exhaust hoovered up by a relative vacuum (reduced pressure) at the top of the chamber. The top and base are arbitrary as the flow could be in an opposite direction. Flushing may also or alternatively by dynamic. For example, a ring or rings (or other shape frame) may be traversed from top to bottom or bottom to top. A ring may collect or exhaust the clearance gas. A ring may be static or may traverse the chamber. A pair or plurality of "rings" may cooperate to exhaust and hoover the gases. A ring may be multi-functional, e.g., exhaust at its bottom or top region with the hoovering and sensing displaced above or below. An edge of the sensor band, e.g., a ring may serve an air curtain to exclude or minimize systemic, random or pseudorandom variability. The ring may include multiple bands of sensors. The ring system may be constructed as a single piece or may include separate bands above or below other rings. Flushing may simply entail passage of time with normal air turnover.

The chamber may feature a bar, ring attachment, or other structure to guide and control a subject. Adjustable shape may act as an alternative or may assist in subject control. A toy may draw a pet along its path. A bar may prevent an animal from backtracking and/or may push the animal along.

When desired, a cleansing or sterilization feature between subject assays may be accomplished using any process that does not damage or hinder chamber function. For example, a sterilizing or flushing gas may be directed against surfaces or may be spread throughout the chamber to minimize cross-contamination between subjects. A misting may be used to distribute or deliver active ingredient which may be vaporized with time, flushing and/or added heat.

Ultraviolet light, especially UV-C, short wavelength, ~200 nm to 280 nm light is less damaging to human tissue than the longer wavelength ultraviolet subdivisions, UV-A and UV-B. Aldehydes are also frequently used as disinfectants, especially for periods in excess of minutes. These must be used with caution to avoid risk to humans and are not a preferred disinfectant. A reduced pressure (vacuum) may contribute to removal of cross contaminating volatiles and/or to serve as a quality check on chamber integrity. $H_2O_2$ and ozone are gaseous disinfecting oxidants available for use as mists or vapors.

Disinfection using heat has an additional benefit of increasing vaporization or the off-gassing of volatile compounds. Heating between subject assays thus is an advantageous factor for reducing carryover from one subject to the next. Temperatures above body temperature (approximately: 39° C.+/−0.5° C. for cattle; 38.4° C.+/−0.7° C. for house cats; 38.5° C.+/−0.5° C. for canines) are preferred. Increased chamber surface or internal temperatures, e.g., the chamber, components or portions of the chamber a maximum or threshold may be brought to a desired temperature such as examples found in literature, including, but not exclusively limited to: about 40° C., 42° C., 45° C., 50° C., 55° C., 60° C., 63° C., 67° C., 70° C., 75° C., 80° C., 85° C., 90° C., 95° C., 97° C., 98° C., 99° C., 100° C., 102° C., 104° C., 105° C., 120° C., 150° C., 180° C., 200° C., 230° C., 250° C., 270° C., etc. Different components of the chamber may be heated to different temperatures. Steam may provide the heating or may be used in conjunction with heating, for example, resistance heating. Heating may be convective from controlled streams of gas, mist or steam; may be inductive, may be resistive or may be accomplished using light, often an infrared (IR) source whose wavelength distribution and peak wavelength are chosen for correspondence with the absorptive, reflective and transmission characteristics of the coating or substrate surface being heated. Drying may be effectively accomplished using IR in about the 3000 to 5500 nm range and about the 6500 to nm range. Water tends to absorb in this range and thus evaporation will not be dependent on the wet surface substrate absorptive properties. Emission in a range of from about 5500 to 10,000 nm is effective for sanitizing or disinfecting a surface. Shorter wave IR may be used, for example, from about 1700 to 4000 nm when proteins or lipids are preferred targets. As a guideline the —OH$^{-1}$ (hydroxyl) group especially present in water, sugars and short alcohols absorbs from about 2700 to 3300 nm; the C—H bond, present in lipids, sugars and proteins absorbs from about 3250 to 3700 nm; and the N—H bond (proteins) absorbs from about 2800 to 3300 nm. An IR and UV source may be used together.

UV-C is preferred for decontaminating/disinfecting because although this C-band is strongly absorbed and damaging to nucleic acids and thus lethal to propagation of microbes exposed to the light, this band is strongly absorbed by skin and fur and fails to penetrate beyond the outer (dead skin) layer of humans or fur of some animals. A mercury-based lighting source is available with a spectral emission about 254 nm, well situated in the UV-C band.

In several circumstances, alcohols including, but not limited to: methanol, ethanol, isopropanol, etc.; acetone; and/or other sterilizing or cleansing liquids may be used alone or in combination when desired—with proper safety precautions following approved safety and exposure protocols.

Following the flushing process, the assay will include fewer results from volatile compounds in the surrounding atmosphere. A second flush or a plurality of subsequent flushes may be initiated to reduce background more thoroughly, such as may be carried in subject's clothes, hair, etc. I A mobile frame may transport NSEs selected to assay one or more VOC(s) or other volatiles of interest. A mobile frame may provide an exhaust directed at the subject to drive volatiles from the subject, for hoovering in a frame. The hoovering and exhausting frame may be the same or may be physically distanced. The exhaust and/or hoovering may alternatively be located in a base or top or cap of the device. For example, the NSEs may be in a ring that draws in the ambient gas to contact the NSE surfaces, while the gas is replenished through the cap or floor.

The device may be multi-compartmentalized. For example, for a live subject, the head may be excluded from the analysis compartment either in a second compartment or left in the ambient atmosphere. When the head or mouth/nose is isolated in a separate compartment—possibly as simple as a mask—breath is available for independent analysis. The breath intake may also be controlled using a mask if controlling the inhaled content of breath is a desired feature. The mask may be used provide, e.g., anesthetic, controlled content of inhaled air (generally $O_2$, $N_2$, $CO_2$, inert gas, temperature, humidity) to monitor and/or control inhalation and exhalation in a combined unitary format.

The device of the present invention provides rapid highly sensitive detection of VOCs in a gas phase sample. Analytical data are then processed using the device's library of algorithms to detect a disease or to answer questions for which the sample was taken. Through machine learning and artificial intelligence, the device is continually developing and improving its algorithms. The system may use non-linear system identification techniques (such as Volterra kernel representations) for continual development.

Through capturing the VOCs in vapor or gas phase to measure the presence, amounts, volume, intensity or strength of signal of multiple VOCs, then classifying each signal as from the organism or the environment and removing foreign VOCs from analysis consideration, the device then outputs a sample's gross output of organism initiated organic compounds for comparison to the signature database to determine characteristics of each subject, especially whether a specific disease (or set of diseases) is present. Diseased animals may be segregated for culling or treatment. Characteristics may suggest which animals are better suited for a set of alternate outcomes. For example, export to a specific country or region, suitability of the animal products for one or more possible markets, e.g., restaurant, fast food, etc. may be flagged using the present invention. The present invention continues to consolidate VOC signature profiles into a library as new sample outputs are presented.

An alternate application of the present device and assay processes is as a screen for exposure. For example, if possible, exposure to a toxic volatile or a hormone is of interest, a simplified assay may be programmed to detect the target substance or its metabolic effects.

In some embodiments, metabolic responses to exposure may be assayed to determine, for example, exposure levels and how the subject is handling (metabolizing) said toxin and may predict when products from such animal would be safe for animal or human consumption. The probe can sense and identify food borne diseases including, but not limited to those having more serious impact on human health e.g., *salmonella, listeria*, hepatitis A, *campylobacter*, norovirus, specific *E. Colis*.

A useful configuration may involve vertically arrayed static strips. Input of moving gas may be from a diverse source such as from the base or cap. Input may be spatially controlled so as to direct continuous or pulsed flow over a progressing portion of the subject over time. The hoovering may coordinately progress in a manner offset from the inflows to collect data progressing spatially over the entire subject. The levels of feed and hoovering may be offset angularly such that the exhausts and hoovering are offset horizontally; the exhaust and hoovering may be offset vertically. Software aware of these timings and offsets will aid in locating the spatial source of the VOCs.

Vertical stripping may include NSE strips in parallel or in combination with lighting strips, directed flow orifices or strips, etc. The strips may be static (not moving with respect to the chamber when a subject is present) or may be tracking with a subject or rotating, for example in a counterclockwise or clockwise direction as selected by the chamber designer, software engineer, operator, or machine learning based algorithm. In some embodiments, the strips may remain static while a subject is manipulated within the chamber, e.g., in accordance with machine or operator instruction to the subject, rotation or partial rotation of the chamber base, advancing through a passageway, etc. A subset of strips may be activated by machine or operator in concert with a predetermined schedule or in response to assay events.

Vertically arranged NSEs may be used in a supportive role in conjunction with one or more sets of horizontal NSEs. For example, the vertical NSEs may activate during a flushing operation following subject enclosure in the chamber. The vertical sensors might monitor the flushing and signal when a stasis condition, e.g., readings indicating successful flushing, occurs. The signal could signal the horizontal sensors to begin monitoring the subject. Mobile wall(s) or ring(s) may slide in or rise from the base or descend from the top, preferably directing air towards the subject while another portion hoovers subject related gaseous content past the NSEs. For quality control the vertical stripped NSEs might remain operational during this alternate assay function and may, in accordance with a predetermined algorithm, modulate the rate of movement of one or more assay ring(s), select individual NSEs or subgroups of NSEs to be active, adjust sensitivity of an NSE or subgroup of NSEs, adjust amount of gas inputting or intensity of vacuuming to optimize chamber performance. The vertical movement may be reversed in response to collected data, perhaps to confirm or refine analysis by rereading a subject body area as a repeated assay with or without sensor adjustment.

The device may be used periodically by or on a specific subject to, for example, provide a timeline showing changes such as maturation, pregnancy progress, growth stage, milk production patterns, disease progression, efficacy food modifications, effect of treatment activities, clearance of drugs, etc. The period between such assessments is determined in accordance with desires/needs of a marketer, trainer or veterinarian, and/or conditions of the subject. Where relevant, especially for pets or in a barn, a daily assessment may be made using a probe available in the home or barn. This might be used in analogy to taking a temperature every morning to determine peak fertilities, and alternatively may be useful for avoiding disruption by animals in heat or for preparation for breeding. The device may include additional features such as a reader (e.g., to detect an animal's identification tag or mark), a scale, body fat, $O_2$ consumption, estrus hormones, temperature, heart rate, etc. Such daily or otherwise frequent check may be used for example, to plan the day's training or other activities or to address nutrient deficiencies or excesses.

Some embodiments feature an interconnected system of devices, for example, devices sited in a city, county, state, etc.; port of entry; zoo; boarding kennel; racetrack; etc. Together such interconnections form a more robust machine learning platform that may identify similar anomalies across a plurality of machines. Data collected over the interconnected system would be merged and continuously analyzed to recognize new patterns. Disease detection would be accelerated as these anomalies are flagged. Novel doping regimens may be discovered for possible regulation. The large data sets can be analyzed with anonymity, with subject location or identity only available in accordance with relevant regulations. This interconnected system is also applicable to obtain an early notice alarm in chemical defense or bio-defense platforms. Veterinary medical records, agricultural databases and in some cases, associated human medical records, can be used to improved analysis and reported results.

Poor feeding management of cows can lead to shorter, lower yielding lactations and increased calving interval, low quality or lower amounts of beef, mistiming of product to market. The probe can reduce these cost impacts.

Devices of the present invention may be incorporated as part of triage operations. One configuration may allow the device to maneuver so that the opening communicates with a selected exit pathway or corridor. Healthy animals suitable for human consumption might be directed along one line while extremely desired animals are advances to premium outlets or possibly for breeding. Identifying most fertile periods increases efficiencies of breeding programs. Optimal timing for breeding purposes is especially advantageous where artificial insemination is unavailable. In the dairy industry, the choice and quantity of feed at each milking can be instantaneously assessed as the cows queue through a walkway for milking. Each cow's use of stored energy can be assessed by monitoring VOCs associated with fat and protein breakdown. With either natural or synchronized estrus, the VOCs can be used to more accurately the end of estrus and monitor progress to ovulation so that artificial insemination (or breeding, if desired) can be timed for optimal probability of success. The estrus cycles leading to the insemination estrus cycle can be monitored and strength of the estrus cycle and viability of the ovum can be considered for scheduling the insemination event (choosing this estrus or a later one as well as the most fertile hours for insemination success). During gestation and lactation, especially when VOCs suggest the calf is female and may be a possible herd replacement, the assay data and algorithms may be used to arrive at a desired compromise between milk production and calf growth. Algorithms may include data on dairy sales and seasonal demand to optimize revenue. During the dry period, feed mix, and caloric intensity can be adjusted using VOC data to minimize the harvesting of the cow's energy stores and maximize female calf growth.

Optimal nutrition may be targeted using probe system algorithms that may include specific herd, breed, pedigree, previous ovulation and missed ovulation cycles, historic pregnancy data, etc. Optimized timing for insemination is another attribute that can be accessed using data and analysis of the present devices. A chamber configured as a breeding stall in a breeding farm facility can optimize determination of mare receptiveness to the breeding event. Such chamber may be used to reduce encounters with a teaser stud and thereby reduce risk of injury to horses and handlers. Determining the most receptive time for bringing in the stallion can increase foaling rate and thus increase stud efficiency and income. The thresholds for such delineations can be set by a human or by algorithm developed in advance or in accordance with machine learning. A robust flush/sanitation/disinfection/decontamination may be practiced following an assessment of a likely exposure to a pathogen. A less robust flush/etc. may be practiced following assessment of lower risk. The selection of cleansing processes may be predetermined, may be under operator control or may be interactive in accordance with a predetermined or adaptable machine learning based procedure.

An alternative configuration has the NSEs stable, that is not moving within the device, but collecting and assaying the flowing gas. The position of the exhaust gas distributor, taking into account the flow rate can provide localization information with respect to the source of VOC(s).

The device as described above is a preferred configuration as an upright standing or moving subject moving will present a maximal surface area for VOC emission to the chamber detectors. For some purposes, the chamber may provide a surface upon which a subject may be laid flat and possibly rotated. The chamber itself may be maneuverable to accept vertical or packaged subjects, such as birds. Capacity for a handler to join the subject within the chamber is another design option.

The invention claimed is:

1. A chamber configured in size to contain a subject, said chamber comprising:
   a barrier isolating an internal gaseous environment for surrounding said subject from the volume outside the chamber;
   said barrier incorporating at least one portion to allow ingress and egress of said subject;
   an internal array of nanosensor elements (NSEs) for sensing volatile compounds;
   a gas directing mechanism that moves gas across NSEs in said internal array;
   a system for collecting data from said NSEs; and
   a system for compiling and analyzing said data.

2. The chamber of claim 1 wherein said volatile compounds comprise volatile organic compounds (VOCs).

3. The chamber of claim 1 wherein said gas directing mechanism comprises a system for propelling a gas towards said subject.

4. The chamber of claim 3 wherein said system for propelling comprises a source of gas at elevated pressure and an orifice to release said gas.

5. The chamber of claim 3 wherein said system for propelling operates in parallel to said internal array is distributed in a vertical configuration.

6. The chamber of claim 1 wherein said gas directing mechanism comprises a ringed shaped system for propelling a gas toward said subject.

7. The chamber of claim 6 comprising a plurality of ringed shaped systems, at least one of said plurality comprising at least a first array of NSEs, and at least one of said plurality comprising a system to propel a gas towards said subject.

8. The chamber of claim 1 wherein said gas directing mechanism comprises a system for feeding or drawing a gas across at least a portion of said array of NSEs.

9. The chamber of claim 8 wherein said system for feeding or drawing a gas across at least a portion of said array of NSEs comprises a vacuum creating device.

10. The chamber of claim 1 wherein said gas directing mechanism that moves gas across NSEs comprises at least one motive force selected from the group consisting of: pressure differential, acoustic drive, electrostatic effect, plasma actuation and photon momentum.

11. The chamber of claim 1 comprising a field-effect transistor NSE.

12. The chamber of claim 1 wherein said system for collecting data is configured to sense movement of at least one electron.

13. The chamber of claim 1 wherein said system for collecting data comprises measurement correlated with a plurality of zones of a chamber.

14. The chamber of claim 1 wherein said system for collecting data comprises longitudinal data measurements.

15. The chamber of claim 14 wherein said longitudinal data measurements track a progress selected from the group consisting of those related to: animal development; food maturation, aging or ripening; milk production; estrus cycle; and pharmaceutical clearance.

16. The chamber of claim 1, wherein the chamber comprises in a geometric shape Non-Uniform Rational Bicubic Splines (NURBS).

17. The chamber of claim 1 featuring a moving conveyor, standway or walkway.

18. The chamber of claim 1 further comprising at least one feature selected from the group consisting of: pressure control, humidity control, temperature control, noise reduction, controlled lighting, variable wall opacity, scent distribution, digital recording and/or playback, sound system, audio instructions, video instructions, three-dimensional body mapping (3D).

19. The chamber of claim 1 wherein said subject is inanimate.

20. The chamber of claim 1 wherein said subject is a human associate with a potential subject animal.

21. The chamber of claim 1 further comprising a mask apparatus to distinguish the subject's gas intake from the gas in the surrounding chamber.

22. The chamber of claim 1 further comprising a head enclosure or mask apparatus to distinguish the gas exhaled by the subject from the gas in the surrounding chamber.

23. The chamber of claim 21 further comprising a head enclosure or mask apparatus to distinguish the gas exhaled by the subject from the gas in the surrounding chamber.

24. The chamber of claim 23 wherein said head enclosure or mask apparatus to distinguish the gas inhaled by the subject from the gas in the surrounding chamber and said mask apparatus to distinguish the gas exhaled by the subject from the gas in the surrounding chamber are unitary.

25. The chamber of claim 1 wherein said analyzed chamber data includes an instruction optimizing breeding functions.

26. The chamber of claim 1 wherein said analyzed chamber data includes an instruction optimizing feeding the subject.

27. The chamber of claim 1 wherein said barrier comprises a gas.

28. The chamber of claim 27 wherein said gas barrier is formed by an air curtain or by spatial separation of subjects.

29. The chamber of claim 2 wherein said internal array of nanosensor elements (NSEs) for sensing volatile organic compounds (VOCs) is zoned to access separate data elements from a plurality of zones.

30. The chamber of claim 29 wherein at least one zone comprises a torso or underarm area.

31. The chamber of claim 1 wherein said system for compiling and analyzing said data features a comparative system comparing a subject's data to a database, recognizing similarities, tagging and ranking similarities and providing a report to an operator or designated report recipient.

32. The chamber of claim 31 wherein said system is dynamically updated following machine learning protocols.

33. The chamber of claim 1 further comprising interface components that receive data from an external database.

34. The chamber of claim 33 wherein said external database is maintained by a monitoring agency.

35. The chamber of claim 34 wherein said monitoring agency is governmental.

36. The chamber of claim 34 wherein said monitoring agency is private.

37. The chamber of claim 33 wherein said database comprises data types selected from the group consisting of: medical records and agricultural databases.

38. The chamber of claim 1 further comprising interface components that receive information from system that has compiled received data from a plurality of devices.

39. The chamber of claim 38 wherein said information is continuously updated.

40. The chamber of claim 1 further comprising interface components that transmit data to a system receiving data from a plurality of devices.

41. The chamber of claim 1 further comprising interface components that transmit data to a remote server.

42. The system of claim 41 wherein said remote server is selected from the group consisting of: a personal server, an institutional server, a proprietary server and a cloud server.

43. A stall sized and shaped chamber comprising:
restraining barriers to immobilize a horse sized animal;
at least one of said barriers comprising a flanking wall to roughly parallel the length of said animal;
at least one internal array of field effect transistor (FET) nanosensor elements (NSEs) for sensing volatile compounds released by an animal in said chamber;
a computational system to collect, compile, store and analyze data resulting from said at least one internal array of field effect transistor (FET) nanosensor elements; and
an alert signaling system that signals an impending ovulation.

44. A two sided chamber configured as a walkway or sluice, said chamber comprising:

two side walls to control motion of an animal;
a reader to scan tagging associated with an animal progressing through said walkway or sluice;
at least one of said walls outfitted with at least one array of field effect transistor (FET) nanosensor elements (NSEs) for sensing volatile compounds released by an animal in said chamber;
a computational system to collect, compile, store and analyze data resulting from said at least one internal array of field effect transistor (FET) nanosensor elements;
a reporting component integrated in or connected to said computational system;
said reporting component interfaced with said reader to identify said animal in said walkway or sluice;
said reporting component interfaced with a database associating identity of animal with lactation status; and
said reporting component also interfaced with a feed delivery system to accept and to act on reports delivered to said feed delivery system.

* * * * *